United States Patent [19]

Schenck et al.

[11] Patent Number: 5,201,312
[45] Date of Patent: Apr. 13, 1993

[54] ANTENNAE FOR HIGH-RESOLUTION MAGNETIC RESONANCE IMAGING OF THE EYE

[75] Inventors: John F. Schenck, Schenectady, N.Y.; Steven P. Souza, Williamstown, Mass.; David R. Eisner, Schenectady, N.Y.

[73] Assignee: General Electric Company, Schenectady, N.Y.

[21] Appl. No.: 939,381

[22] Filed: Aug. 19, 1992

Related U.S. Application Data

[63] Continuation of Ser. No. 707,998, May 23, 1991, abandoned, which is a continuation of Ser. No. 452,176, Dec. 18, 1989, abandoned.

[51] Int. Cl.$^5$ ............................................. A61B 5/055
[52] U.S. Cl. ................................ 128/653.5; 324/318
[58] Field of Search ..................... 128/653.2, 653.5; 324/318, 322

[56] References Cited

U.S. PATENT DOCUMENTS

| | | | |
|---|---|---|---|
| 4,543,959 | 10/1985 | Sepponen | 128/653 |
| 4,587,492 | 5/1986 | Laudermilch | 324/318 |
| 4,617,936 | 10/1986 | Malko | 128/653 |
| 4,672,972 | 6/1987 | Berke | 324/318 |
| 4,680,549 | 7/1987 | Tanttu | 324/318 |
| 4,684,894 | 8/1987 | Bliehall | 324/318 |
| 4,721,913 | 1/1988 | Hyde et al. | 128/653 |
| 4,739,269 | 4/1988 | Kopp | 324/318 |
| 4,841,249 | 6/1989 | Duerr et al. | 324/318 |

FOREIGN PATENT DOCUMENTS

| | | |
|---|---|---|
| 0314359 | 5/1989 | European Pat. Off. . |
| 3822185 | 1/1989 | Fed. Rep. of Germany . |
| 0232189 | 8/1987 | France . |
| 2153086 | 8/1985 | United Kingdom . |
| 2210982 | 6/1989 | United Kingdom . |

OTHER PUBLICATIONS

Magnetic Resonance in Medicine, vol. 3, pp. 270–281, 1986 "Application of Anatomically Shaped Surface Coils in MRI at 0.5 T".

*Primary Examiner*—Ruth S. Smith
*Attorney, Agent, or Firm*—Lawrence P. Zale; Marvin Snyder

[57] ABSTRACT

An antenna for NMR imaging of the eye of a patient includes a small circular or oval surface coil which is locatable immediately adjacent to the eye of the patient and supported by a member having a shape contoured to fit in the region between the zygomatic and supraorbital arches of the face. The supporting member may be a disc supporting a whole-eye surface coil anterior of the eye, or may be a contact-lens-like member supporting a fine wire surface coil substantially in contact with the anterior orbital aspect.

4 Claims, 2 Drawing Sheets

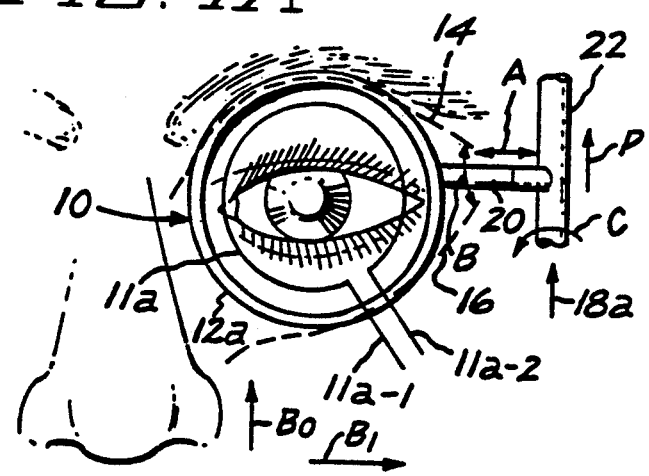
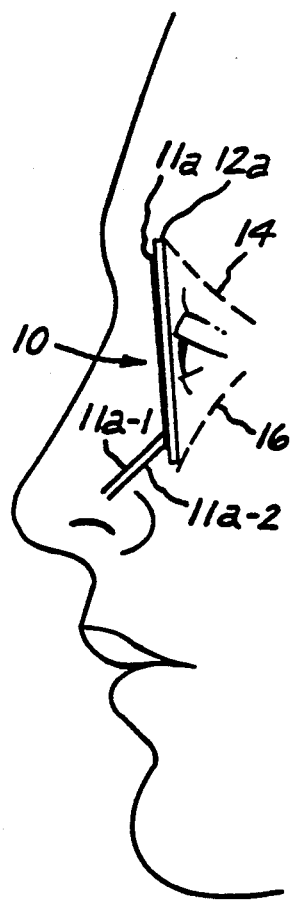
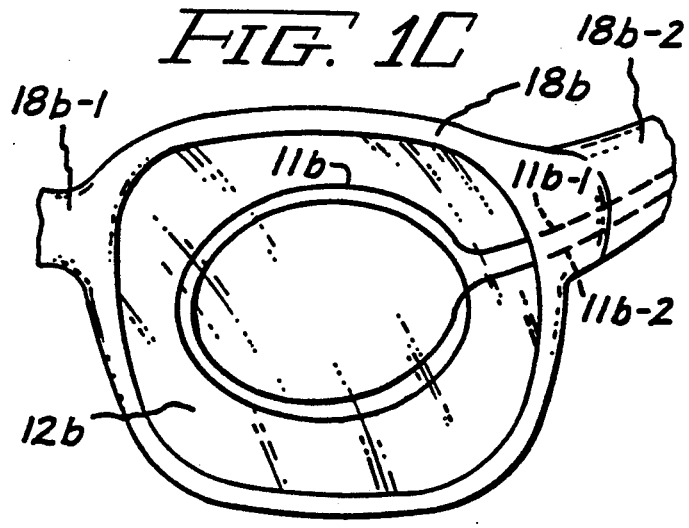

ANTENNAE FOR HIGH-RESOLUTION MAGNETIC RESONANCE IMAGING OF THE EYE

This application is a continuation of application Ser. No. 07/707,998, filed May 23, 1991 now abandoned, which is a continuation of application Ser. No. 07/452,176 filed Dec. 18, 1989, now abandoned.

BACKGROUND OF THE INVENTION

The present invention relates to nuclear magnetic resonance (NMR) imaging and, more particularly, to novel antennae for high-resolution NMR imaging of the eye of a patient.

It is known that high-contrast magnetic resonance imaging of the human eye is possible. However, diagnosis of eye diseases by use of NMR imaging has been prevented due to certain technical limitations, so that radiologists frequently continue to use computed tomography examinations for eye studies in cases where magnetic resonance imaging (MRI) may potentially provide a higher contrast and more detailed image. In addition to the higher image quality potentially offered by MRI examinations, it is known that the x-ray dose attendant to computerized-tomography scanning is sufficiently large so that, in most cases, follow-up studies on any given patient are precluded. Conversely, MRI studies appear to be repeatable as often as necessary for a given patient. Accordingly, it is highly desirable to overcome the following technical limitations for NMR imaging of the human eye: present sensitivity and signal-to-noise ratio (SNR) characteristics of the receiver coil must be increased to permit rapid high-resolution imaging of small structures, such as the lens and the like, within the eye; and any such receiver coil utilized for eye imaging must avoid the hitherto-encountered difficulties in awkwardness in placement of such reception coils in position over the eye and in maintenance in the placed position, even while being more easily tolerated by the patient during the MRI scanning process. Accordingly, reception coils with sufficiently high sensitivity, great ease of placement and support, and patient tolerance, are highly desirable.

Prior Art

Previous eye-imaging antennas have utilized surface coils of circular or elliptical (mask) form, which surface coils were designed to fit over the forehead and anterior facial areas of the patient being imaged. Such coils generally are of a typically large size, having an approximate 10–20 centimeter measured diameter. Due to spatial constraints imposed by the (zygoma) cheek bone and other boney structures in the forehead and nose of the patient, the sensing elements of previous coils are located at least 5 centimeters from the anterior eye structures (the lens and the like).

BRIEF SUMMARY OF THE INVENTION

In accordance with the invention, an antenna for NMR imaging of the eye of a patient, includes a small circular or oval surface coil which is locatable immediately adjacent to the eye of the patient and supported by a member having a shape contoured to fit in the region between the zygomatic and supra-orbital arches of the face. The supporting member may be a disc supporting a whole-eye surface coil anterior of the eye, or may be a contact-lens-like member supporting a fine wire surface coil substantially in contact with the anterior orbital aspect, for high-resolution imaging of the cornea, lens and like interocular structures.

Accordingly, it is an object of the present invention to provide novel antennae for high-resolution NMR imaging of a patient's eye.

This and other objects of the present invention will become apparent upon a reading of the following detailed description, when considered in conjunction with the associated drawings.

BRIEF DESCRIPTION OF THE DRAWINGS

FIG. 1A and 1B are respective front and side views of a portion of the face of a patient undergoing NMR ocular imaging utilizing a first presently preferred embodiment of our novel surface coil;

FIG. 1C is a portion of an optical prosthesis device carrying a second embodiment of our novel high-resolution NMR ocular imaging surface coil;

DETAILED DESCRIPTION OF THE INVENTION

Figure 1D:
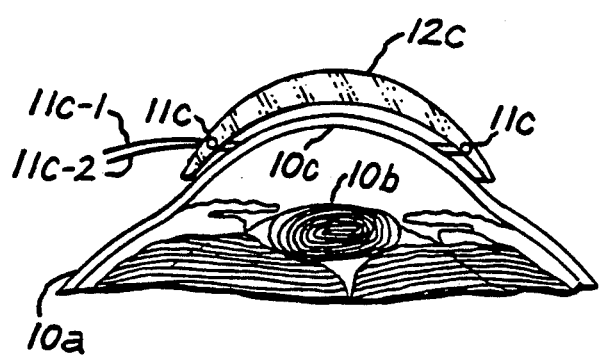
FIG. 1D is a sectional view of a portion of an eye of another presently preferred surface coil embodiment for providing high-resolution NMR imaging of interocular structures.

Referring initially to FIGS. 1A and 1B, an eye 10 of a patient is imaged by use of NMR imaging techniques in which the patient is within the magnetic field $B_o$ of the NMR imaging apparatus (not shown, but itself well known) with an excitation RF field $B_1$ being provided either by a whole-body or whole-head RF coil (also not shown, but well known to the art) or by an ocular surface coil antenna, such as a first coil 11a (or coils 11b/11c in FIGS. 1C and 1D/1E, respectively). The excited nuclei within the various portions of the eye re-radiate RF signals which are received by one of the antennae 11a, 11b, 11c of the present invention. If the antennae 11a, 11b, 11c are only used for reception purposes, a blocking network (active or passive, as well known to the art) may be required; an associated tuning and/or matching networks, external to the antenna 11a, 11b or 11c, may also be needed (and, while not shown, is also well known in the art). In a presently preferred first embodiment, a substantially planar surface coil 11a is a single-turn loop of conductive material supported by a non-magnetic, insulative member, such as member 12a in FIGS. 1A/1B so shaped and dimensioned as to be positionable anteriorly adjacent to the eye 10, and generally between the supra-orbital arch 14 of the patient's frontal bone and the zygomatic, or infra-orbital, arch 16 of the malar (cheek) bone. This position locates the surface coil 11a a near to the eye (e.g. within about 1 cm. of the surface of the eye), so that the field-of-view of the reception coil is limited to substantially the eye volume, thus enhancing image resolution. A typical coil 11a may have a diameter or major axis of between about 3 and about 5 cm. and an inductance in the 50–200 nanohenry range, so that a high-Q resonant circuit can be produced, centered around the coil, to enhance the signal-to-noise ratio (SNR) of the NMR response signal.

Enhanced SNR allows achievement of one or both of the aforementioned increased resolution or reduced image acquisition time (by reducing the number of signal averages and/or the sequence repetition time $T_R$). The coil and member 12a are maintained in position by a rotatable support means 18a, including a support arm 20, extendable in the direction of arrows A toward and away from the patient and rotatable in the direction of arrows B and having a first end joined to member 12a and a second end joined to a support member 22. The arm 20 can be rotated about member 22, in the direction of arrows C, and moved up and down member 22, in the direction of arrows D, so that member 12a can be placed as required, relative to the eye 10, and maintained thereat, once the patient's head is firmly held by cushion/strap restraints. Ideally, the coil is placed within several millimeters of the patent's eyelid. The coil 11a connects to a pair of coil leads 11a-1 and 11a-2, which may be dressed as required.

Referring now to FIG. 1C, another presently preferred surface coil antenna 11b has a plurality of turns, arranged in a substantially oval shape and supported upon a member 12b, such as a transparent glass substrate utilized in place of a lens in one opening of a locating means 18b shaped as a conventional eyeglass frame. In this embodiment, the eyeglass frame nose-bridge piece 18b-1 and sidearm piece 18b-2 contact the respective nose and ear of the patient and relatively fixedly maintain antenna coil 11b in a location anterior to the eye of the wearer. Coil lead wires 11b-1 and 11b-2 may be secured to the surface of, or implanted within, the insulative material of member 12b and frame 18b, and may be passed along the sidearm piece 18b-2, in manner so as to undergo minimal mechanical stress, thereby allowing relatively fine conductors to be utilized, if required.

Figure 1E:
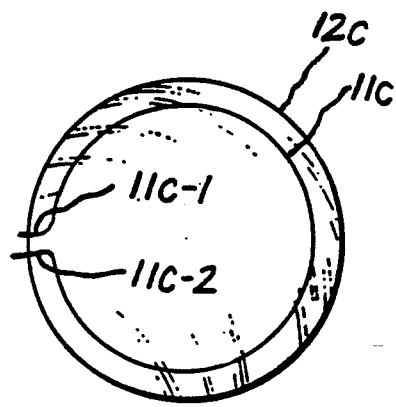
FIG. 1E is a front view of the embodiment of a contact-lens coil of FIG. 1D.
Figure 1F:
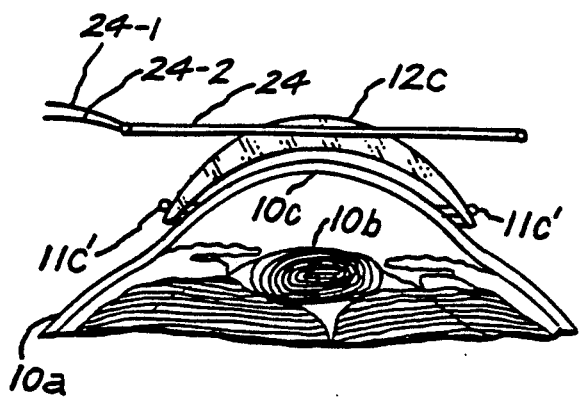
FIG. 1F is a sectional view of a portion of an eye of another surface coil embodiment having an inductive coupled coil for providing high resolution NMR imaging of intraocular structures.
Figure 1G:
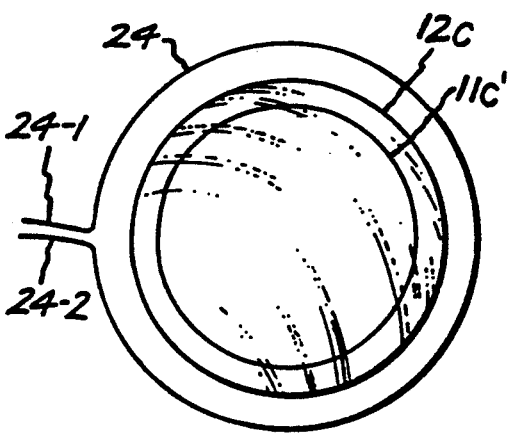
FIG. 1G is a front view of the embodiment of a contact-lens coil of FIG. 1F.

It will be noted that the eye-imaging antenna coils 11a and 11b are relatively large, and are so positioned as to be best suited for whole eye imaging. In cases where MRI examination of the fine structure, such as the anterior sclerotic layer 10a, lens 10b, cornea 10c as shown in FIGS. 1D and 1F and the like, are the objects primarily to be imaged, a smaller single turn surface coil 11c of FIGS. 1D and 1E, and coil 11c' of FIGS. 1F and 1G, located as close to the exterior of cornea 10c as practical, is desirable. FIG. 1D shows a surface coil 11c as a single loop conductor, of either circular or oval shape, embedded within as shown in FIGS. 1D and 1E, or upon the exterior surface of (as shown by substitute coil 11c' as shown in FIGS. 1F and 1G), a contact-lens-like supportive member 12c. Member 12c can be fabricated of any desirable hard or soft contact lens material, and may have a curvature suitable to the anterior corneal curvature of the patient's eye being imaged. Coil 11c of FIG. 1E shows an embodiment having a single loop of a thin (0.5 mm. or thinner) wire with an approximate oval shape being less than the size of the contact-lens-like member 12c. When the contact-lens-like member 12c is applied directly to the sclera of the patient's eye, thin coil wire extensions 11c-1 and 11c-2 of FIGS. 1D and 1E may extend therefrom to suitable terminations, which may be taped adjacent to the patient's eye, and the like. Alternatively, the receive signal from embedded antenna surface coil 11c, or lens-surface-positioned antenna surface coil 11c', as shown in FIGS. 1F and 1G, may be inductively coupled into a second coil 24 having coil lead lines 24-1 and 24-2, positioned adjacent to the eye (possible in manner similar to the eye-adjacent coils 11a or 11b). It will be understood that, because of the small size of the lens-born coil 11c/11c', printed circuit techniques may be utilized to construct the actual conductive loop within, or upon the surface of, the supporting member 12c.

While several presently preferred embodiments of our novel invention have been described in detail herein, many modifications and variations will now become apparent to those skilled in the art. It is our intent, therefore, to be limited only by the scope of the appending claims and not by the specific details and instrumentalities presented by way of explanation herein.

What we claim is:

1. An antenna adapted for NMR imaging for an eye of a patient, comprising:
    a surface coil having at least one turn of a conductive wire arranged in one of circular and oval shape; and
    means for locating and maintaining the surface coil adjacent to an anterior surface of said eye and in an orbital region of said patient bounded by the zygomatic and super-orbital arches;
    wherein said means for locating includes a contact-lens-like member supporting the surface coil,
    the contact-lens-like member being adapted for holding the surface coil adjacent to a sclerotic portion of said eye.

2. The antenna of claim 1, wherein the surface coil is fabricated upon an exterior surface of said contact-lens-like member.

3. The antenna of claim 1, wherein the surface coil is embedded within said contact-lens-like member.

4. The antenna of claim 1, further comprising a pickup coil inductively coupled to said surface coil.

* * * * *